US006870948B2

(12) United States Patent
Jun et al.

(10) Patent No.: US 6,870,948 B2
(45) Date of Patent: Mar. 22, 2005

(54) METHOD AND APPARATUS FOR NUMERICALLY ANALYZING GRAIN GROWTH ON SEMICONDUCTOR WAFER USING SEM IMAGE

(75) Inventors: Chung-sam Jun, Hwasung-gun (KR); Sang-Mun Chon, Seongnam-si (KR); Sang-Bong Choi, Suwon-si (KR); Kye-Weon Kim, Suwon-si (KR); Sang-Hoon Lee, Suwon-si (KR); Yu-Sin Yang, Yongin-si (KR); Sang-Min Kim, Seoul (KR); Sang-Kil Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 700 days.

(21) Appl. No.: 09/977,238

(22) Filed: Oct. 16, 2001

(65) Prior Publication Data

US 2002/0072133 A1 Jun. 13, 2002

(30) Foreign Application Priority Data

Oct. 19, 2000 (KR) ........................................ 2000-61717

(51) Int. Cl.$^7$ ........................ G06K 9/00; H01L 21/8242
(52) U.S. Cl. ........................ 382/145; 382/147; 438/253
(58) Field of Search .................................. 382/145, 147, 382/194; 438/207–208, 231–232, 14, 16, 253, 396

(56) References Cited

U.S. PATENT DOCUMENTS

| | | | | |
|---|---|---|---|---|
| 5,910,019 A | * | 6/1999 | Watanabe et al. | ............ 438/488 |
| 5,985,497 A | * | 11/1999 | Phan et al. | .................... 430/30 |
| 5,989,969 A | * | 11/1999 | Watanabe et al. | ............ 438/381 |
| 5,990,002 A | * | 11/1999 | Niroomand et al. | ......... 438/636 |
| 6,171,737 B1 | * | 1/2001 | Phan et al. | .................... 430/30 |
| 6,228,740 B1 | * | 5/2001 | Niroomand et al. | ......... 438/398 |
| 6,366,688 B1 | * | 4/2002 | Jun et al. | ..................... 382/145 |
| 6,385,020 B1 | * | 5/2002 | Shin et al. | ..................... 361/15 |
| 6,522,776 B1 | * | 2/2003 | Ehrichs | ...................... 382/144 |
| 6,743,645 B2 | * | 6/2004 | Kubota et al. | ................ 438/14 |
| 6,801,650 B1 | * | 10/2004 | Kikuchi et al. | ............. 382/145 |

* cited by examiner

Primary Examiner—Samir Ahmed
Assistant Examiner—Brian Le
(74) Attorney, Agent, or Firm—Volentine Francos & Whitt, PLLC

(57) ABSTRACT

A method and apparatus for numerically analyzing a growth degree of grains grown on a surface of a semiconductor wafer, in which the growth degree of grains is automatically calculated and numerated through a computer by using an image file of the surface of the semiconductor wafer scanned by an SEM. A predetermined portion of a surface of the wafer is scanned using the SEM, and the scanned SEM image is simultaneously stored into a database. An automatic numerical program applies meshes to an analysis screen frame and selects an analysis area on a measured image. Thereafter, a smoothing process for reducing an influence of noise is performed on respective pixels designated by the meshes using an average value of image data of adjacent pixels. A standardization process is then performed, based on respective images in order to remove a brightness difference between the measured images. After comparing standardized image data values of the respective pixels with a predetermined threshold value, the number of pixels whose standardized image data value is greater than the threshold value is counted. The growth degree of grains on the surface of the wafer is calculated by numerating a ratio of the counted number with respect to a total number of the pixels contained within the analysis target image.

31 Claims, 21 Drawing Sheets

THRESHOLD VALUE=200, GROWTH DEGREE OF HSG=8%

THRESHOLD VALUE=121, GROWTH DEGREE OF HSG=68%

THRESHOLD VALUE=89, GROWTH DEGREE OF HSG=84%

GROWTH TIME=60 S, GROWTH DEGREE OF HSG=36%

GROWTH TIME=100 S, GROWTH DEGREE OF HSG=54%

GROWTH TIME=140 S, GROWTH DEGREE OF HSG=66%

METHOD AND APPARATUS FOR NUMERICALLY ANALYZING GRAIN GROWTH ON SEMICONDUCTOR WAFER USING SEM IMAGE

BACKGROUND OF THE INVENTION

1. Field of the Invention

The present invention relates to a method and an apparatus for analyzing and evaluating a surface state of a semiconductor wafer, and more particularly, to a method and an apparatus for accurately and quantitatively analyzing/evaluating a growth state of grains on the surface of a semiconductor wafer, in which the grain growth is automatically calculated using an image file of the surface of the semiconductor wafer that is scanned by scanning electron microscopy (SEM).

2. Description of the Related Art

As semiconductor devices become smaller, the elements of the device, such as a capacitor, also become correspondingly smaller. Since the capacitance of the capacitor is proportional to a surface area of a capacitor electrode, semiconductor manufacturers and designers must somehow compensate for the reduced size and capacitance of these smaller capacitors. Accordingly, a focus of the manufacturing process is to obtain a larger surface area for the capacitor electrode.

One typical manufacturing method for increasing the surface area of the capacitor electrode is to grow hemispherical grains (HSGs) on a surface of the capacitor electrode. One particular manufacturing method increases the surface area of the electrode itself by forming a one cylinder stack (OCS)—type capacitor electrode on which the HSGs are grown. The introduction of the OCS process combined with the HSG process increases the surface area of the capacitor electrode, thereby obtaining a large capacitance of the capacitor electrode.

The surface area of the OCS-type capacitor is smaller in an upper distal portion thereof and larger along the sidewalls thereof. During the manufacturing process for forming the OCS-type capacitor, the degree of HSG growth directly affects the ability to achieve a target capacitance, and therefore, a method for measuring a thickness of the HSGs is used and monitored. However, that method is ineffective in those cases where a polysilicon thin film, on which the HSGs of a measurement test portion may be grown, is etched after introducing the OCS process.

To overcome this problem, a method for measuring light reflectivity within a cell has been proposed, but this method suffers a drawback in that it lacks the ability to precisely discriminate between elements of the semiconductor device.

Meanwhile, a scanning electron microscopy (SEM) method is widely used to precisely scan the surface state of the semiconductor wafer and analyze a manufacturing defect. When used in conjunction with measuring the growth degree of HSGs on a semiconductor wafer, the SEM simply scans the growth state of the HSGs grown on the OCS-type capacitor and then displays a scanned image. Therefore, the operator must directly view the displayed image and determine the growth degree of the HSGs empirically. As can be expected, such an empirical measuring method needs much time and effort, and additionally, it is difficult to accurately evaluate the quantitative growth degree of the HSGs because of the vagaries and inconsistencies inherent in a process involving human intervention.

SUMMARY OF THE INVENTION

It is therefore an object of the present invention to provide a method and an apparatus for automatically analyzing a growth degree of grains on a surface of a semiconductor wafer using image data generated by scanning the surface of the semiconductor wafer through a scanning electron microscopy (SEM).

In accordance with an aspect of the present invention, there is provided a method for numerically analyzing a growth degree of grains on a surface of a semiconductor wafer, including: selecting a numerical target zone in an image file for numerating the growth degree of grains on a specific portion of the surface of the semiconductor wafer, the image file being generated by scanning the specific portion on the surface of the semiconductor wafer using a scanning electron microscopy (SEM); performing a standardization with respect to an image data of respective pixels disposed within the selected numerical target zone to attain standardized image data values; comparing the standardized image data values of the respective pixels with a predetermined threshold value and counting the number of pixels whose standardized image data value is greater than the threshold value; and numerating the growth degree of grains on the surface of the numerical target zone by calculating a ratio of the number of the counted pixels with respect to the number of total pixels disposed within the numerical target zone.

In other aspects the image may be displayed on a monitor, and the operator may have the capability to designate different numerical target zones in the displayed image in order to numerate the growth degree of grains on specific portions of the surface of the semiconductor substrate.

Before performing the standardization with respect to the image data, a smoothing process may be implemented. The smoothing process smoothes the image data of the respective pixels disposed within the numerical target zone using an average value of image data of adjacent pixels in order to remove noise that may be caused when an analog signal is converted into a digital signal.

The standardization is performed using the following equation:

$$NC_{ij} = \left(\frac{C_{ij} - C_{\min}}{C_{\max} - C_{\max}}\right) \times K$$

where, $NC_{ij}$ is a standardized image data value of a pixel disposed at a point (i,j), $C_{ij}$ a non-standardized image data value of the pixel disposed at the point (i,j), $C_{min}$ is a minimum value of image data within the numerical target zone, $C_{max}$ is a maximum value of image data within the numerical target zone, and K is a constant, which represents the number of total gradations of the monitor.

Still further, the method may include forming mesh lines for dividing a screen of the monitor into a plurality of sub areas on the displayed image, thereby enabling the operator to designate at least one sub area as the numerical target zone.

In accordance with another aspect of the present invention, there is provided an apparatus for numerically analyzing a growth degree of grains on a surface of a semiconductor wafer. The apparatus includes a scanning electron microscopy (SEM) for scanning a specific portion of the surface of the semiconductor wafer to generate an image signal. An analog-to-digital conversion section converts the image signal generated by the scanning electron microscopy (SEM) into digital data, and then a computer section stores the digital data as an image file. The computer carries out a sequence of operations including opening the stored image file to automatically select a numerical target zone for numerating the growth degree of grains on the specific portion of the wafer, performing a standardization with respect to image data of respective pixels disposed within the selected numerical target zone, comparing the standardized image data values of the respective pixels with a predetermined threshold value to thereby count the number of pixels whose standardized image data value is greater than the threshold value, and numerating the growth degree of grains on the surface of the numerical target zone by calculating a ratio of the number of the counted pixels with respect to the number of total pixels disposed within the numerical target zone. A display section or screen then displays the calculated ratio.

The computer section can also form mesh lines for dividing the screen into a plurality of sub areas over the displayed image, and allowing an operator to select a numerical target zone by selecting a designated sub area.

It is desirable that, before performing the standardization, the computer section performs a smoothing process for smoothing the image data of the respective pixels disposed within the numerical target zone using an average value of image data of adjacent pixels.

BRIEF DESCRIPTION OF THE DRAWINGS

The above objects and other advantages of the present invention will become more apparent by describing in detail preferred embodiments thereof with reference to the attached drawings in which.

DETAILED DESCRIPTION OF THE PREFERRED EMBODIMENTS

Figure 1:
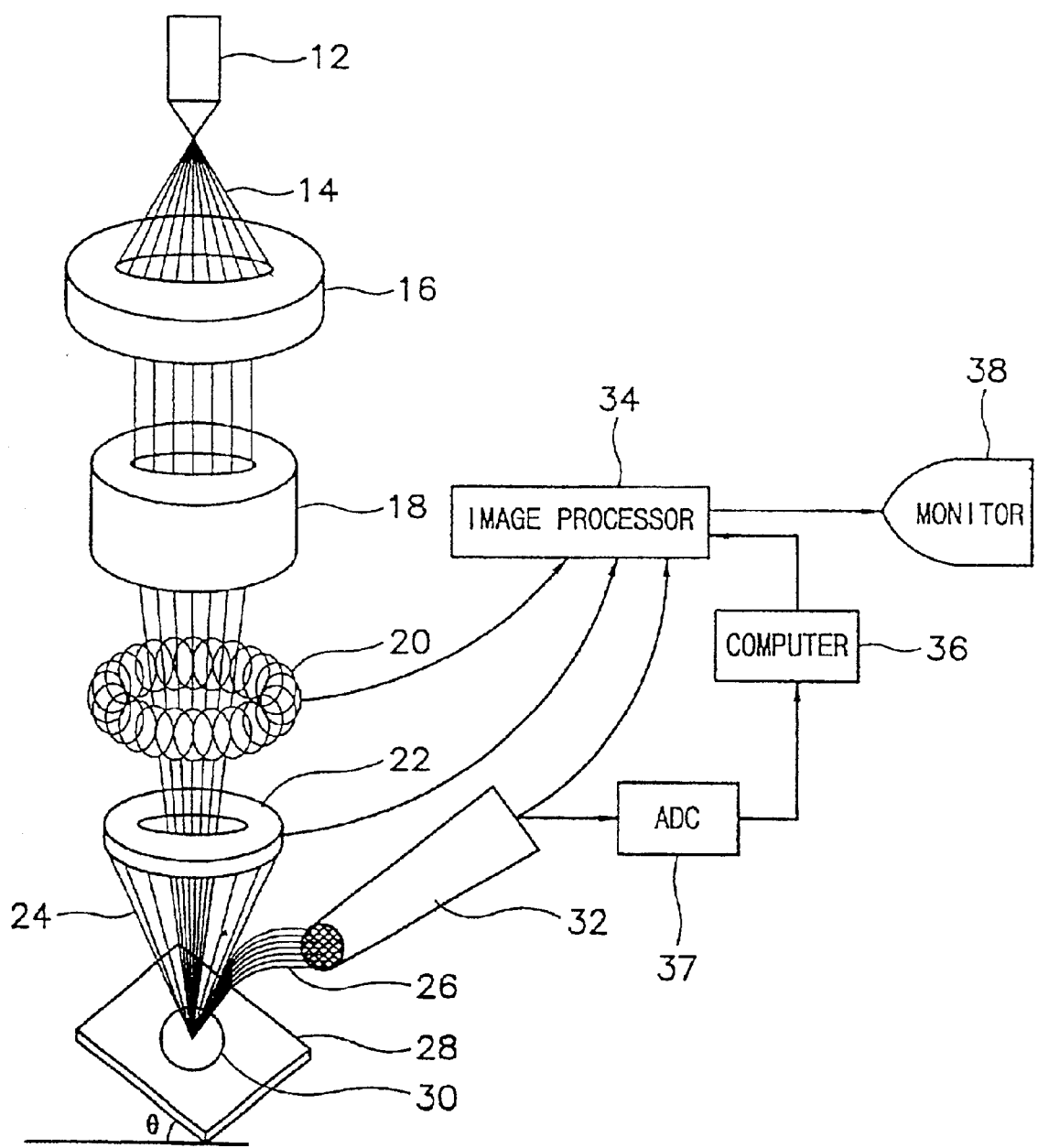
FIG. 1 is an exploded schematic view showing an apparatus for numerically analyzing a growth degree of grains on a surface of a semiconductor wafer in accordance with an embodiment of the present invention.

The present invention will now be described more fully with reference to the accompanying drawings, in which a preferred embodiment of the invention is shown. This invention may, however, be embodied in many different forms and should not be construed as being limited to the embodiments set forth herein. Rather, the embodiments are provided so that this disclosure will be thorough and complete, and will fully convey the concept of the invention to those skilled in the art. In the drawings, the thickness of a layer or region are exaggerated for clarity. It will also be understood that when a layer is referred to as being "on" another layer or substrate, it can be directly on the other layer or substrate, or intervening layers may also be present.

FIG. 1 is a view showing an apparatus for numerically analyzing a growth degree of grains on a surface of a semiconductor wafer in accordance with an embodiment of the present invention. The apparatus can be a scanning electron microscope (SEM) with a built-in computer.

Generally, the SEM has an electron gun for producing electrons, electron lens units, a chamber unit, and display units. The electron lens units include a first condenser lens 16, a second condenser lens 18 and a scanning coil 20. The electron lens units 16, 18 and 20 accumulate and irradiate the electrons produced by the electron gun 12 toward a surface of a specimen 30 to thereby control a magnification of an image. The chamber unit includes a stage 28 for loading the specimen 30 thereon, a backscattered electron detector 22 for detecting backscattered electrons 24, and a secondary electron detector 32 for detecting secondary electrons 26. The stage 28 may be tilted at an angle θ as described later. The display units include an image processor 34, e.g., a scanner, for processing electrical image signals generated by the detectors 22 and 32, and a monitor 38 for displaying the processed image signals on a screen thereof.

Additionally, the SEM further comprises a computer 36 for processing required data and controlling the operation of the SEM, and an analog-to-digital converter 37 for converting an analog signal outputted from the secondary electron detector 32 into a digital signal and providing the digital signal to the computer 36. The SEM is a microscope for forming an image using the secondary electrons 26 and the backscattered electrons 24, which are sputtered when electron beams 14 are irradiated on the surface of the specimen 30, to thereby observe a surface state of the specimen 30.

Figure 2:
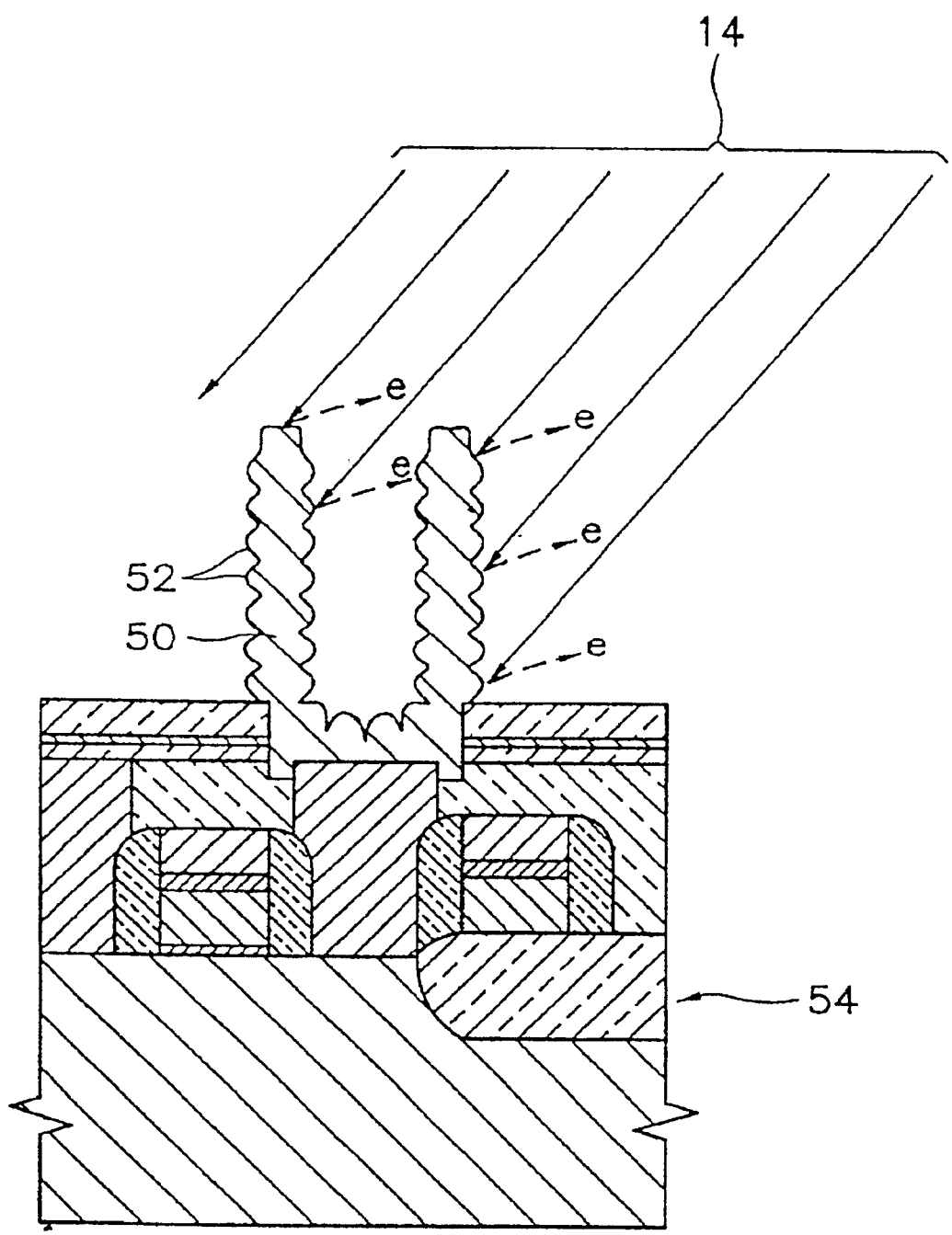
FIG. 2 is a cross-sectional view of an OCS-type capacitor having HSGs grown thereon.

FIG. 2 is a cross-sectional view showing a predetermined portion 54 of an OCS-type capacitor cell 50 in which hemispherical grains (HSGs) are grown on the specimen 30, i.e., a semiconductor wafer.

Initially, in order to perform the method of the present invention, one must scan the surface of the semiconductor wafer, especially that of the capacitor cell 50 to thereby obtain an image data thereof. The scanning procedure is described in greater detail below.

First, if a recipe for an SEM scanning operation is selected, the specimen 30, i.e., the semiconductor wafer, is loaded on the stage 28, and a specific portion to be tested is searched. The optimum magnification and focus are determined while tilting the stage 28, and then, the image is scanned and stored. Unlike a stack-type capacitor, since the surface area of an upper distal portion of the OCS-type capacitor cell 50 is small, it is difficult to accurately determine the growth state of the HSGs only using the image of the upper distal portion. For this reason, it is necessary to obtain a sidewall image of the capacitor cell 50 in which a majority of the HSGs 52 are grown. Therefore, it is preferable that the electron beams 14 should be uniformly incident on the upper portion and the sidewalls of the capacitor cell 50 by tilting the stage 28 to a predetermined angle ($\theta$), e.g., about a 45 degree angle.

The electron beams 14 are produced by applying a high voltage to the electron gun 12. The electrons 'e' emitted from the electron gun 12 are accelerated and concentrated within the electron lens units 16, 18 and 20 due to an acceleration voltage and are then irradiated toward the specimen 30. When the electron beams 14 are irradiated toward the specimen 30, electrons 'e', such as the secondary electrons 26 and the backscattered electrons 24, having various information are emitted. The detectors 22 and 32 detect the backscattered electrons 24 and the secondary electrons 26, respectively, and the detected electrons are converted into an electrical signal. Then, the electrical signal is amplified to thereby generate an analog image signal.

Since the SEM image obtained from the secondary electrons has a deep depth of focus, the SEM image is clear even though the specimen has a rough surface such as a cut section. The image data is transmitted to the monitor 38 through the image processor 34, and the surface image of the specimen 30 is displayed or provided as a photograph by a camera (not shown). Moreover, the image signal is converted into digital data by the analog-to-digital converter 37, and the digital data is stored in the computer 36 in a form of an image file. The image file is linked to the information on a test position and an identification number of a test slot.

Alternatively, rather than storing the backscattered electrons as the image file, the SEM perceives the raw data itself of the backscattered electrons as the electrical signal and stores the data into a memory. The stored data is used as basic data. At this time, it is more useful to perform the above-mentioned process using the image data in the SEM in order to improve an interface with an operator of the equipment.

When the image file for the surface of the specimen 30 is prepared, the growth degree of the HSGs with respect to the OCS-type capacitor cell 50 is automatically numerated. The numerical process is performed by the computer 36 with a built-in numerical program.

Figure 3:
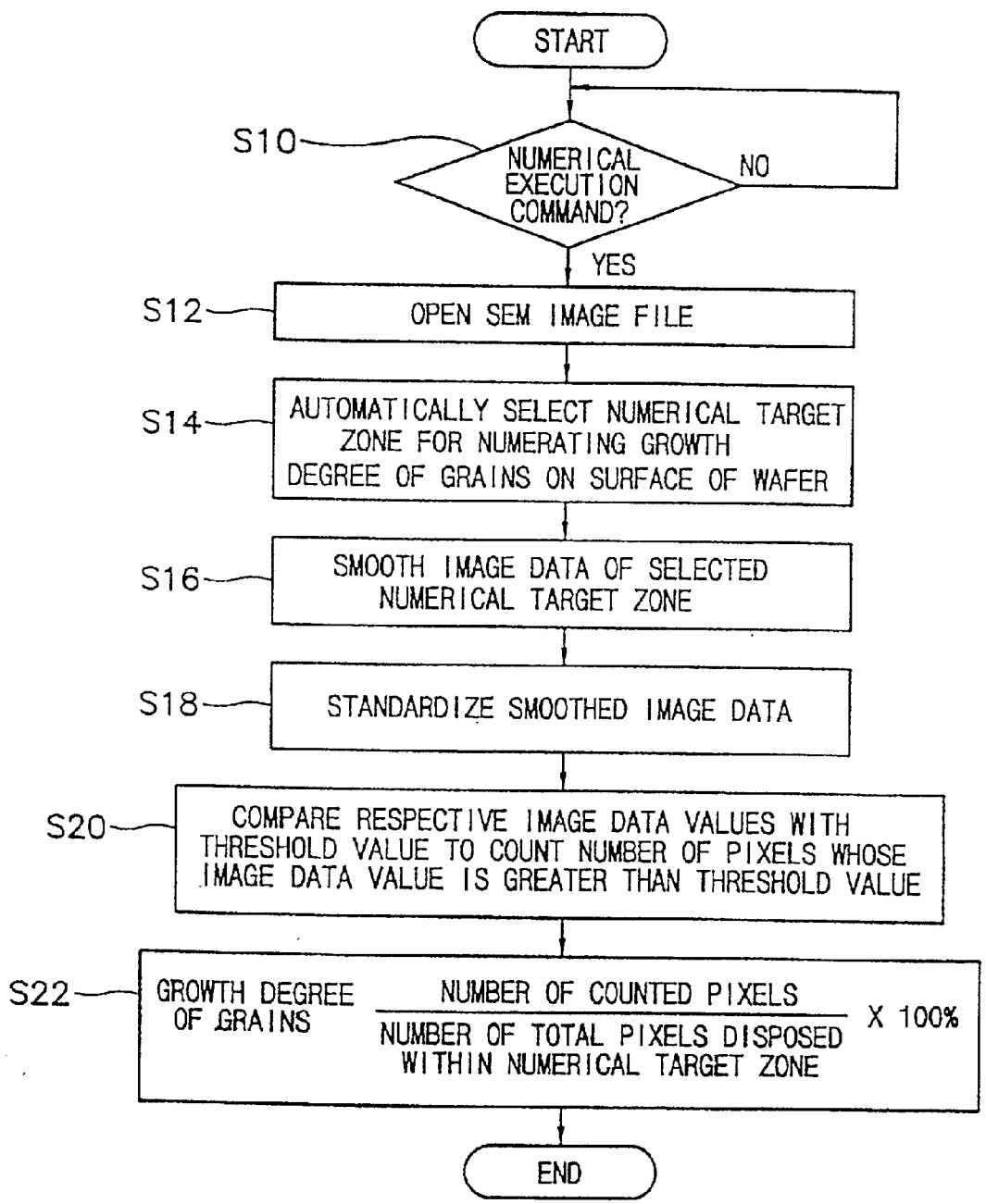
FIG. 3 is a flowchart showing a first numerical algorithm for numerating the growth degree of grains on the semiconductor wafer.
Figure 4:
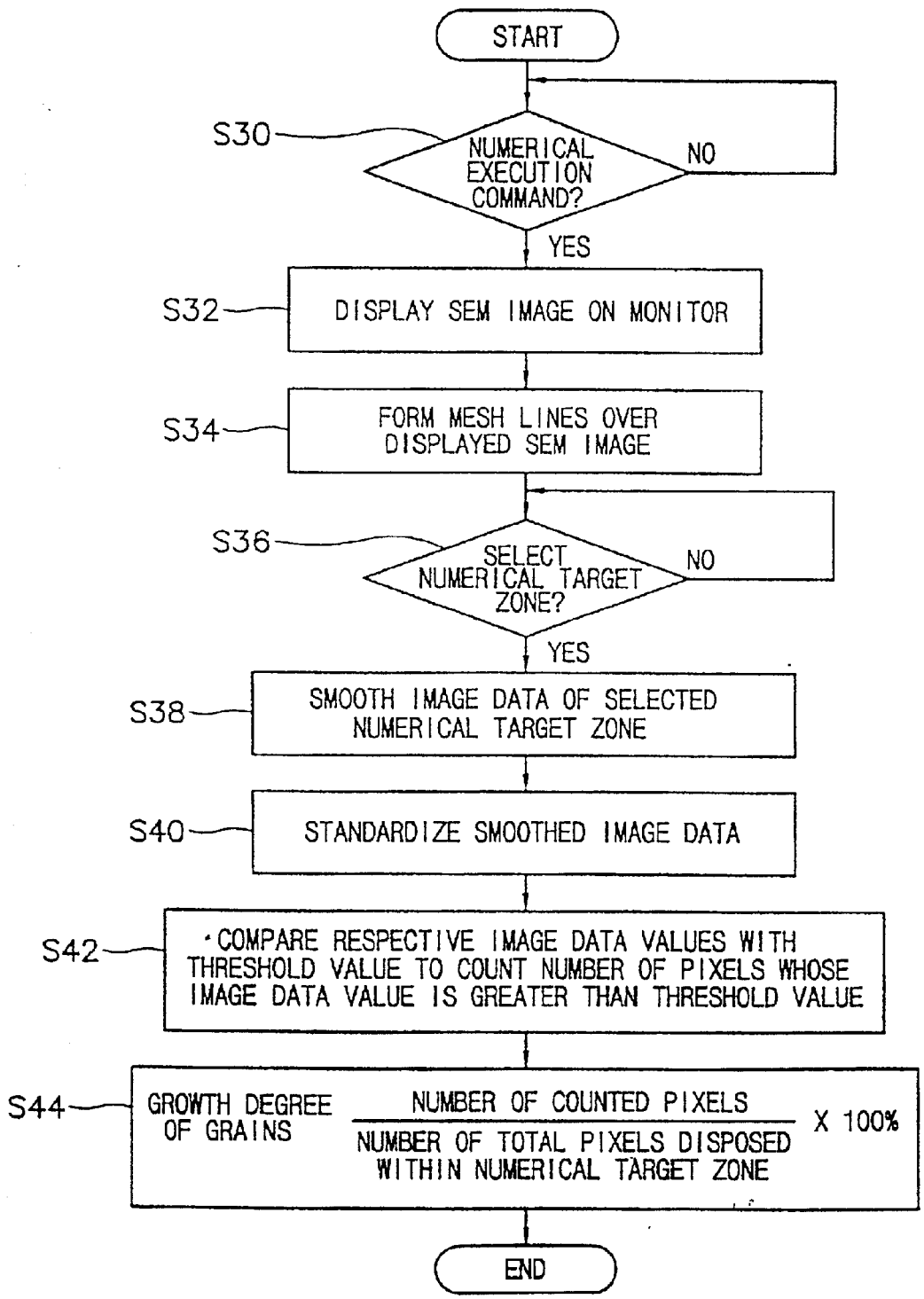
FIG. 4 is a flowchart showing a second numerical algorithm for numerating the growth degree of grains on the semiconductor wafer.

Two numerical algorithms, shown in FIGS. 3 and 4, are proposed as embodiments of the present invention. In the first algorithm of FIG. 3, the program automatically selects the numerical target zone. In the second algorithm of FIG. 4, the operator selects the numerical target zone.

FIG. 3 is a flowchart showing a first numerical algorithm for numerating the growth degree of grains on the semiconductor wafer. Referring to FIG. 3, the operator executes a numerical program on a screen of the monitor 38. At step S10, if a numerical execution command is ordered, a menu for selecting a numerical recipe name on an initial screen is provided to thereby enable the operator to select a desired recipe name. The numerical recipe includes information such as a storage directory of image files to be numerated, an area and a position of the numerical target zone, a threshold value, and information on a directory in which the image files are to be re-stored. The operator selects an image file to be numerated among the recipe files. The computer 36 executes the numerical program in response to the operator's numerical execution command.

At step S12, once the numerical program is executed, the numerical program residing in a memory of the computer 36 reads out the image file to be numerated from memory, which is stored on a hard disk or any other suitable memory storage medium. Then, the image file is opened in order to perform a numerical process, and the following data process is performed.

The numerical process includes a batch processing routine for numerating several image files simultaneously, or an individual processing routine for numerating one image file individually.

In the case of the batch processing, several image files to be numerated are stored in advance in a specific directory of the hard disk or other memory medium, and if necessary, the numerical process is commanded while designating the specific directory. Then, the computer sequentially opens several image files stored in the specific directory, performs the numerical process, and generates a numerical result for the respective image files.

In case of the individual processing, it is possible to perform the numerical process while designating the image files stored in the hard disk or other memory medium one by one. Also, the numerical process is directly performed in a state when the image files are temporarily stored in the memory, i.e., before the image files generated by the SEM are stored into the hard disk, thereby allowing for an intermediate examination of a manufacturing state. Then, when a satisfactory result is obtained, the image files and the numerical result are stored on the hard disk.

At step S14, after opening the image file, the numerical target zone for numerating the growth degree of grains among data of the image file is automatically selected. The image file generated by the SEM can be stored in various file formats. For example, the image data is may be compressed and stored in a tagged image file format (TIFF).

Figure 5:
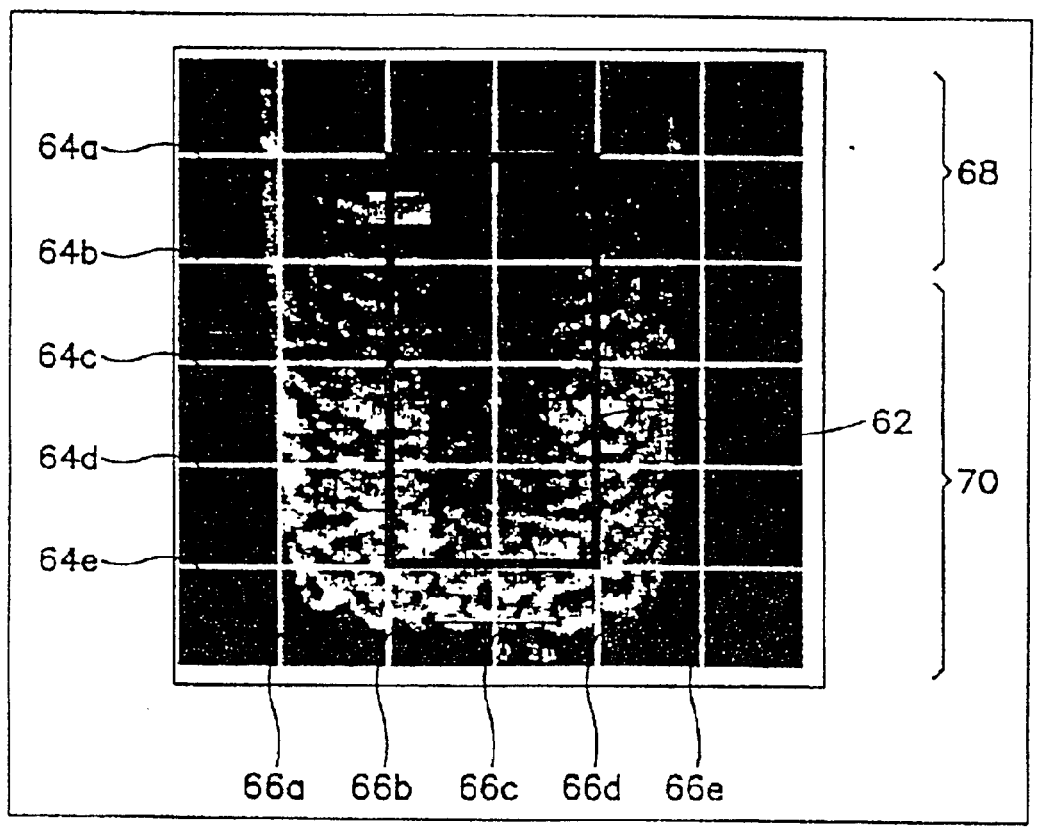
FIG. 5 is a view showing mesh lines formed over an SEM image frame of one OCS-type capacitor cell.

FIG. 5 is a view of an SEM image showing one OCS-type capacitor cell, more particularly, a view of an image showing an upper and lower portion of the OCS-type capacitor. The image was obtained by scanning the OCS-type capacitor cell when the tilt angle $\theta$ of the stage 28 was about 45 degrees. In the SEM image, the image's center-portion numerical target zone, i.e., the OCS-type capacitor cell, is overlapped in the center of the image at the same magnification.

The automatic selection of the numerical target zone is performed through a mesh algorithm. The mesh algorithm is utilized to reduce calculation errors caused by a brightness deviation. In the mesh algorithm, the image is first divided with a certain spacing along the direction of the x-axis and y-axis, thereby obtaining a plurality of sub areas in a mesh form. In FIG. 5, the image is divided into 6 sections at intervals of 80 pixels along the x-axis and the y-axis using five mesh lines 64a–64e and another five mesh lines 66a–66e. Note that at this point of the process, the image division is not seen on the screen of the monitor 38, but the underlying data of the image file is indeed divided in the above-mentioned way.

After dividing the image file, a zone where a numerical calculation is to be performed, i.e., the data, is automatically selected. Although the numerical calculation can be performed with respect to the total image file, it is desirable to select a proper numerical target zone in order to accurately analyze the growth state of the HSG. As can be seen in FIG. 5, since the upper portion 68 of the image and the upper portion of the sidewalls 70 are not as bright as the lower portion of the sidewalls 70, the accuracy of the calculation is lowered. Accordingly, it is desirable that a format for increasing the accuracy of calculation should be implemented by selecting the numerical target zone so as to have a just a small difference in brightness. Accordingly, the numerical target zone is designated by the bold line shown in FIG. 5. The data corresponding to this area 62 is extracted from the image file using coordinate values. That is, the coordinate values corresponding to intersecting points of the mesh lines (64a and 66b, 64e and 66b, 64a and 66d, and 64e and 66d) are compared with coordinate values corresponding to the image data of respective pixels to thereby extract the image data of pixels disposed within the numerical target zone 62 automatically.

Figure 6A:
FIGS. 6A and 6B are views showing magnified SEM images of predetermined upper and lower portions in a numerical target zone shown in FIG. 5, respectively.
Figure 6B:
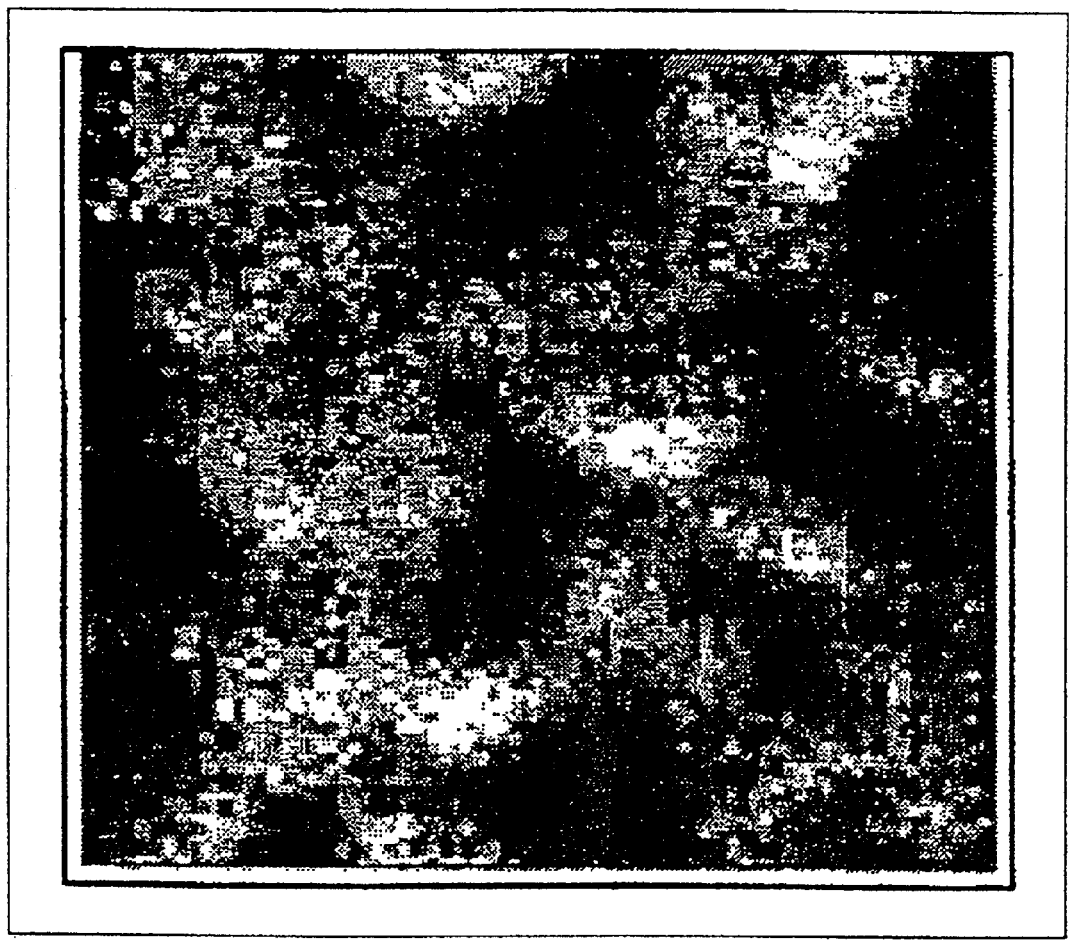
Figure 7A:
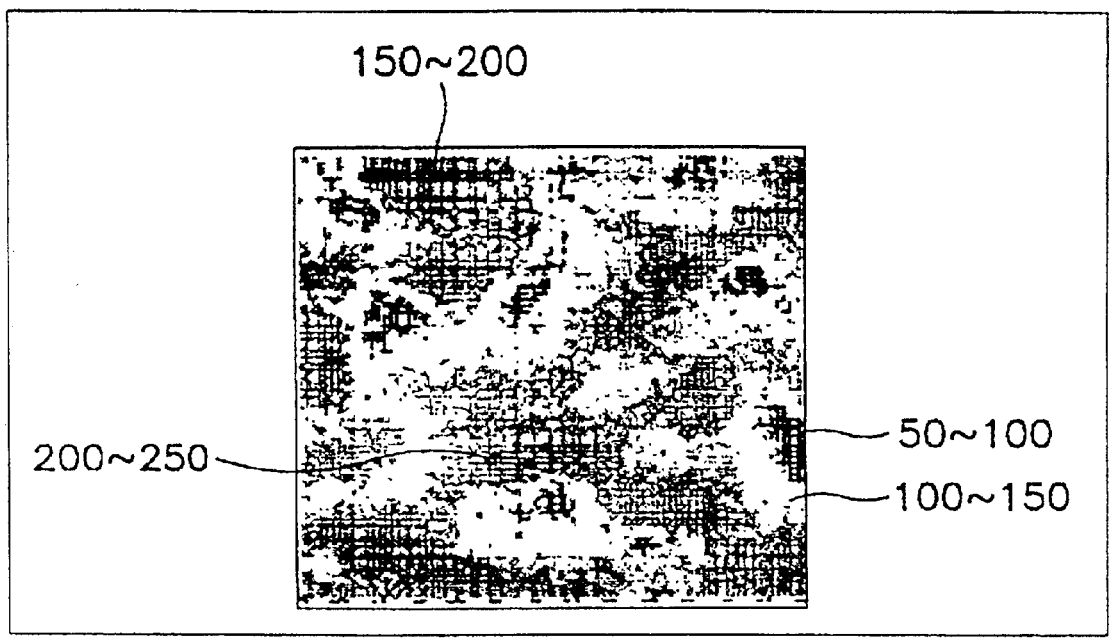
FIGS. 7A and 7B are exemplary views of magnitude distributions when image data values of the SEM images shown in FIGS. 6A and 6B are divided into five grades by changing the image data value from 0 to 250, respectively.
Figure 7B:
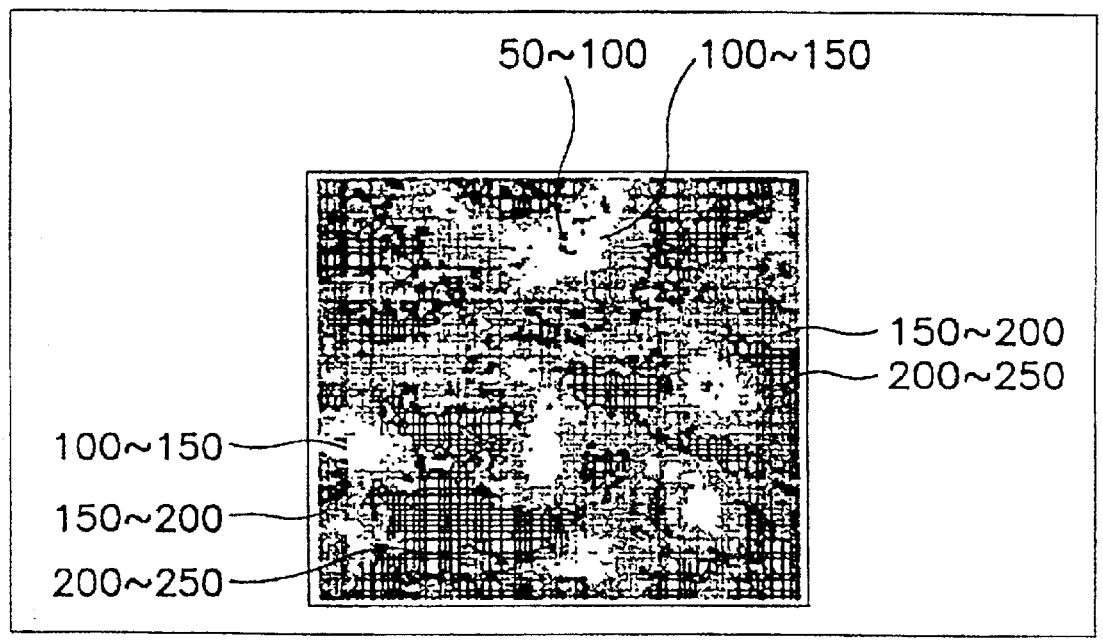

At step S18 (step S16 will be described later), after extracting the data of the numerical target zone, the extracted data is standardized. FIGS. 6A and 6B are magnified SEM images of predetermined upper and lower portions of the numerical target zone 62 shown in FIG. 5, respectively. If the two magnified images shown in FIGS. 6A and 6B are numerated, the distribution of an image data value is significantly changed according to brightness and contrast, as shown in FIGS. 7A and 7B. FIGS. 7A and 7B are views of magnitude distributions when the image data values are divided into five grades by changing the image data value from 0 to 250. If the image having a low brightness shown in FIG. 6A is numerated, there exists many data values of 150 or less. By contrast, if the image having a high brightness shown in FIG. 6B is numerated, there exist many data values of 150 or more. In such a state, it is difficult to objectively determine the growth degree of the HSGs. Therefore, it is advantageous to determine the growth degree of the HSGs by standardizing respective image data values of pixels disposed within the numerical target zone 62, using a maximum value and a minimum value of the image data thereof.

The standardization with respect to the image data of respective pixels disposed within the numerical target zone 62 is performed using the following $$NC_{ij} = \left(\frac{C_{ij} - C_{min}}{C_{max} - C_{max}}\right) \times K \quad \text{(Eq. 1)}$$

where, $NC_{ij}$ is a standardized image data value of a pixel disposed at a point (i,j), $C_{ij}$ a non-standardized image data value of the pixel disposed at the point (i,j), $C_{min}$ is a minimum value of image data within the numerical target zone, $C_{max}$ is a maximum value of image data within the numerical target zone, and K is a constant. It is desirable that the constant K is set to the number of total gradations of the monitor. For example, if the number of the gradations of the monitor is 256, the constant K is also set to 256.

Figure 8A:
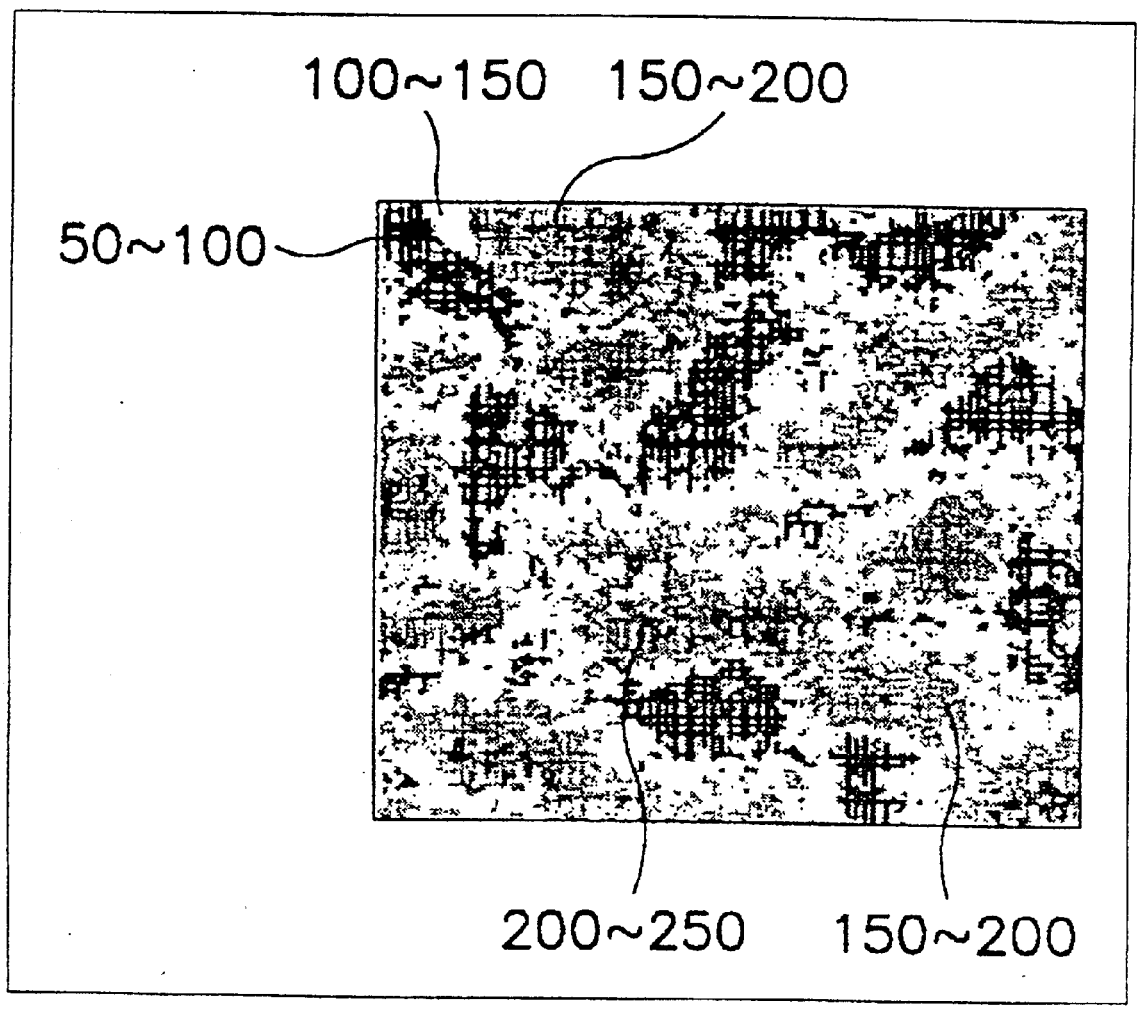
FIGS. 8A and 8B are exemplary views of images obtained after standardizing the image data of the SEM images shown in FIGS. 6A and 6B, respectively.
Figure 8B:
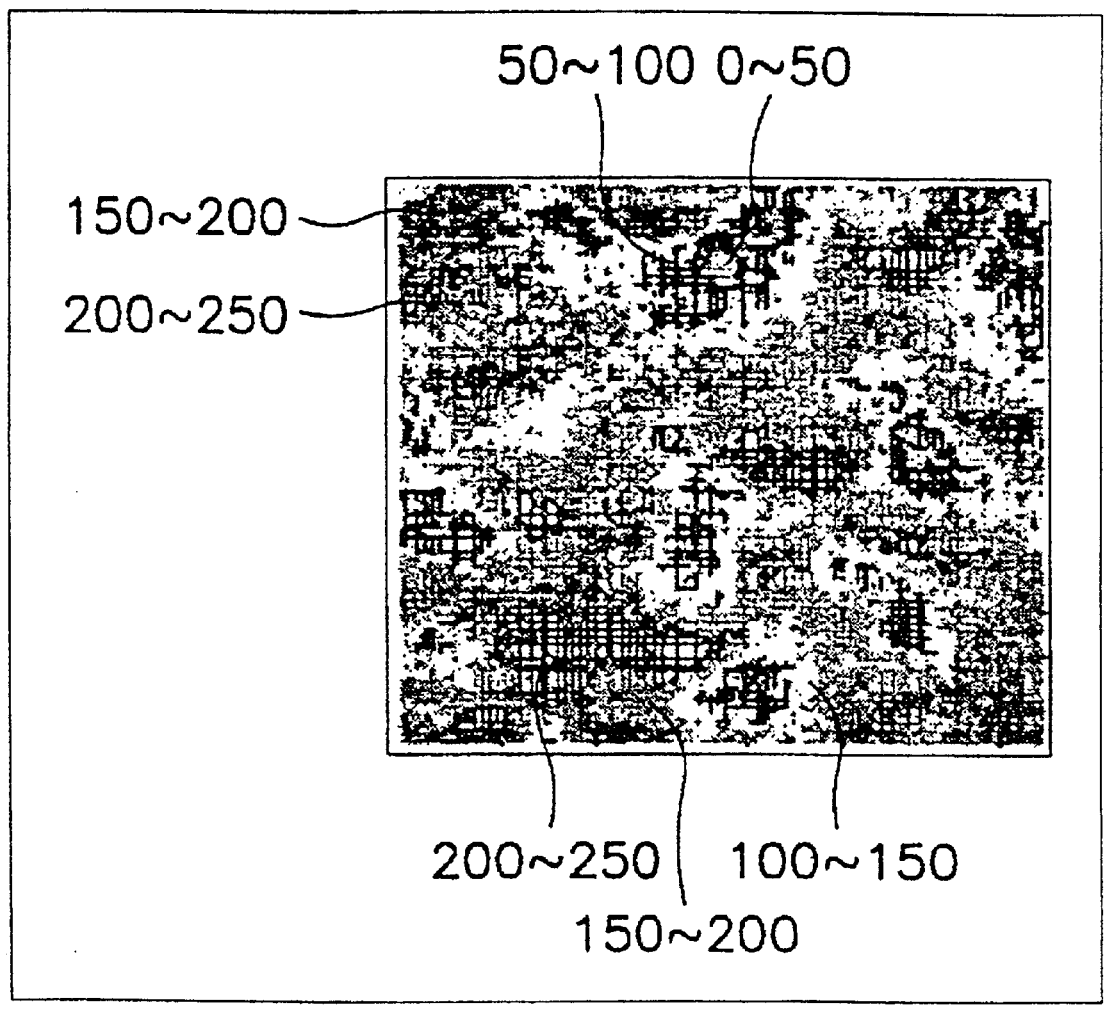

If all the pixel data of the pixels disposed within the numerical target zone 62 are standardized using Equation 1, the standardized data value $NC_{ij}$ has a value between 0 and K. FIGS. 8A and 8B are views of SEM images obtained after standardizing the SEM image shown in FIGS. 6A and 6B, respectively. Referring to FIGS. 8A and 8B, it can be seen that numerated brightness grades are distributed much more uniformly.

Meanwhile, prior to the standardization process, it is preferable to first perform a smoothing process (step 16) with respect to the image data of the respective pixels. Although the smoothing process is not always required, it is desirable in order to obtain a more accurate numerical calculation result. Recall that the standardization is performed using the maximum value and the minimum value of the pixel data within the numerical target zone. When the maximum value and the minimum value are determined, if a digitalization noise component is contained in the image, the possibility of error increases due to the influence of the noise on the maximum value and the minimum value. This problem can be solved using the smoothing process for minimizing the noise component contained in the image data of the respective pixels.

The smoothing process changes the image data of the respective pixels disposed within the numerical target zone using an average value of the image data of adjacent pixels. One smoothing method is performed using the following equation:

$$AC_{ij} = \frac{\sum_{k=0,l=0}^{k=2,l=2} C_{i+j,j+k}}{9} \quad \text{(Eq. 2)}$$

where, $AC_{ij}$ is an average image data value of a pixel disposed at a point (i,j), and $C_{i+j,\ j+k}$ are non-standardized image data values of the adjacent pixels. Using the above-mentioned smoothing equation, the image data of 8 adjacent pixels and the average value of their own image data are calculated. Then, the previous image data of the pixels to be smoothed are replaced with the calculated average value. The smoothing process is applied to all the pixels disposed within the numerical target zone 62 to complete the smoothing process. Note that the number of the pixels contained when the average value of the image data is calculated need not always be 9. If the pixels to be smoothed can be removed, it is possible to calculate the average value of only several pixels, e.g., 4 pixels, among the 8 adjacent pixels.

At step S20, the standardized image data values of the respective pixels are compared with a predetermined threshold value. Then the number of pixels is counted for which the standardized image data value is greater than the threshold value.

Finally, at step S22, the growth degree of grains on the surface of the numerical target zone is determined or numerated by calculating the ratio of the number of the counted pixels with respect to a number of total pixels disposed within the numerical target zone.

Referring now to the second algorithm of FIG. 4, the difference with the algorithm of FIG. 3 is that the operator selects the numerical target zone in FIG. 4, rather than it being automatically selected. Certain of the steps in both algorithms are the same, so a further detailed discussion of those steps will be skipped where appropriate.

Referring to FIG. 4, at step S30, the operator executes a numerical program on a screen of the monitor 38. If a numerical execution command is ordered, a menu for selecting a numerical recipe name on an initial screen is provided to thereby enable the operator to select a desired recipe name. Similar to step S10, the numerical recipe includes information such as a storage directory of image files to be numerated, an area and a position of the numerical target zone, a threshold value, and information on a directory in which the image files are to be re-stored. The operator selects an image file to be numerated among the recipe files. The computer 36 executes the numerical program in response to the operator's numerical execution command.

At step S32, the computer 36 reads out the data of the opened image files and provides it to the image processor 34, thereby displaying the SEM image on the monitor 38. For example, the SEM file as shown in FIG. 5 is displayed on the monitor 38.

Additionally, at step S34, a plurality of mesh lines 64a–64e and 66a–66e are formed for dividing the screen of the monitor 38 into a plurality of sub areas, in which the mesh lines are overlapped over the displayed image. The operator selects the numerical target zone using any suitable input device, such as a mouse (not shown), on the screen of the monitor 38 displaying the SEM image of the scanned OCS-type capacitor cell overlapped with the mesh lines.

At step S36, by monitoring the operator's selection, the computer 36 searches the image data corresponding to the selected numerical target zone of the image file stored in the memory. For example, if the 8 sub areas within the bold line 62 shown in FIG. 5 correspond to the operator selected numerical target zone, the image data contained within the numerical target zone 62 are extracted from the image file using the coordinate data. According to this method, since the operator directly views the image displayed on the screen and selects the numerical target zone, the correctness of the selected numerical target zone may be more evident compared with the automatically selected first numerical algorithm. However, since the operator must directly select the numerical target zone, the degree of automation is decreased, and the time and effort involved in the process are increased.

Figure 9A:
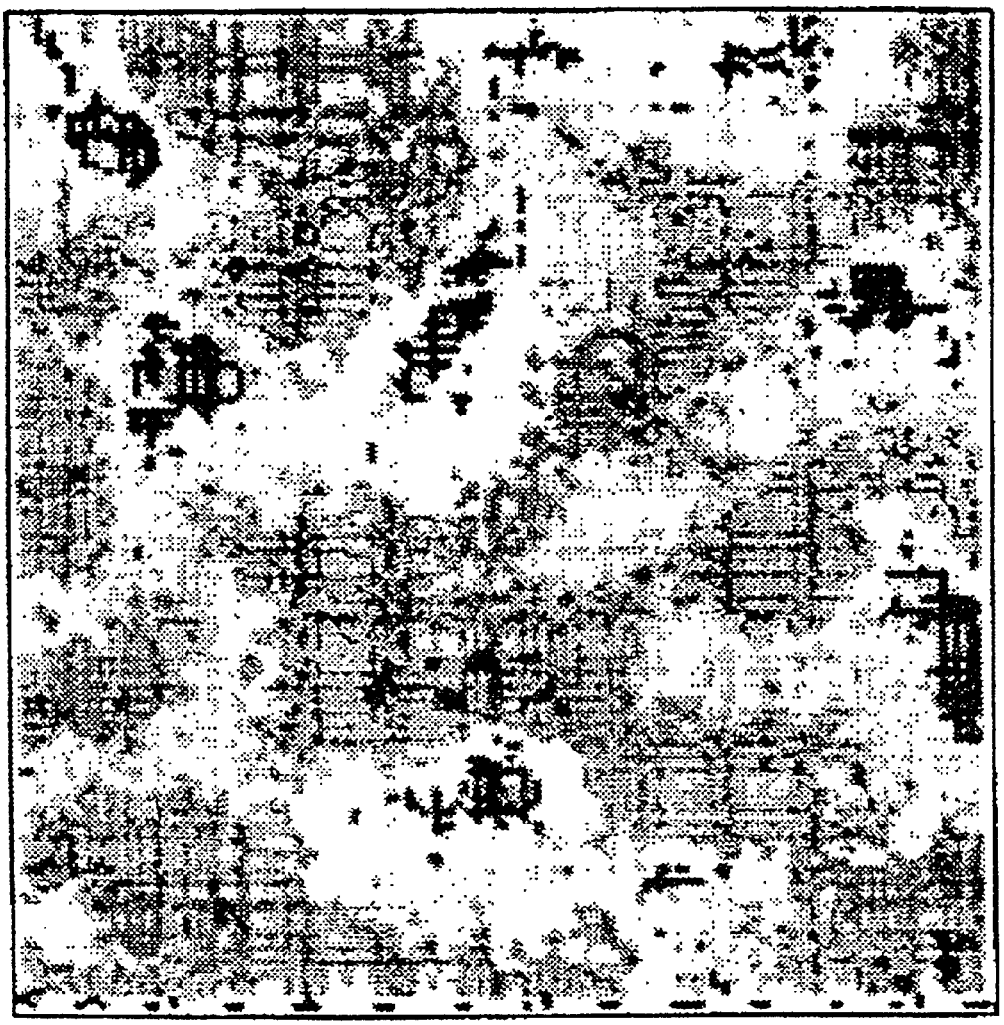
FIG. 9A is an exemplary view of an image before performing a smoothing process.
Figure 9B:
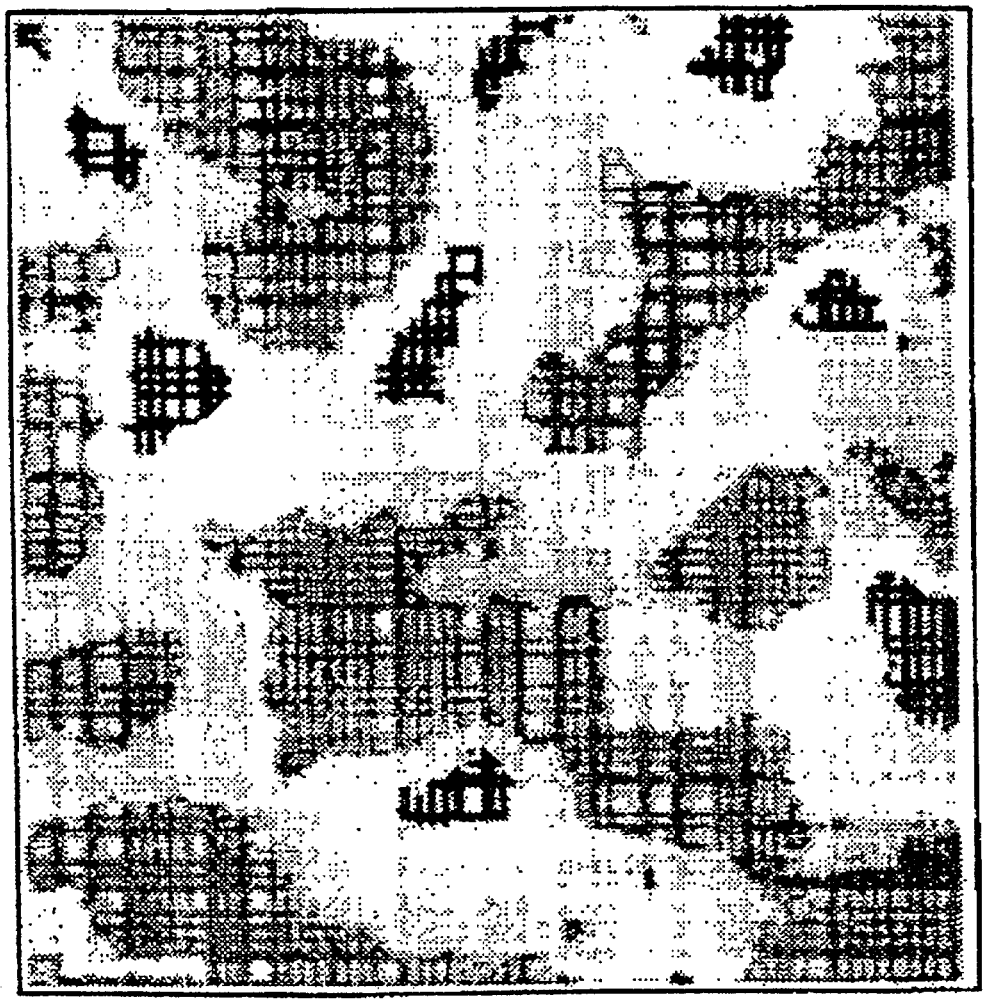
FIG. 9B is an exemplary view of an image after performing a smoothing process.

At step S38, after extracting the image data of the numerical target zone, the smoothing process is performed with respect to the extracted image data, similar to step S16 previously described. FIG. 9A is an exemplary view of an image before performing a smoothing process, and FIG. 9B is an exemplary view of an image after performing a smoothing process.

Figure 10A:
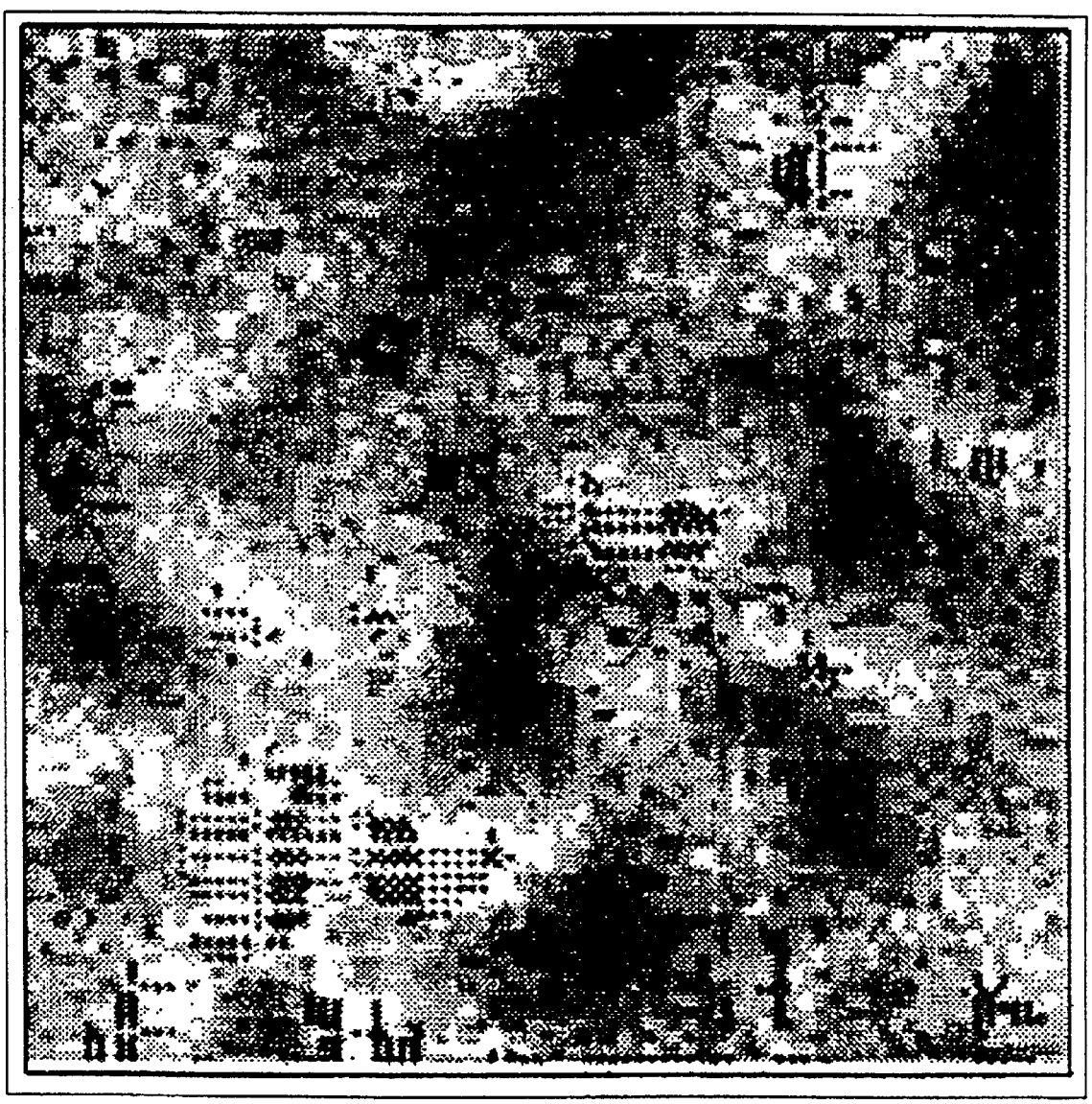
FIGS. 10A to 10C are exemplary views of images showing a calculated value of the growth degree of the HSGs and a growth state of the HSGs, respectively.
Figure 10B:
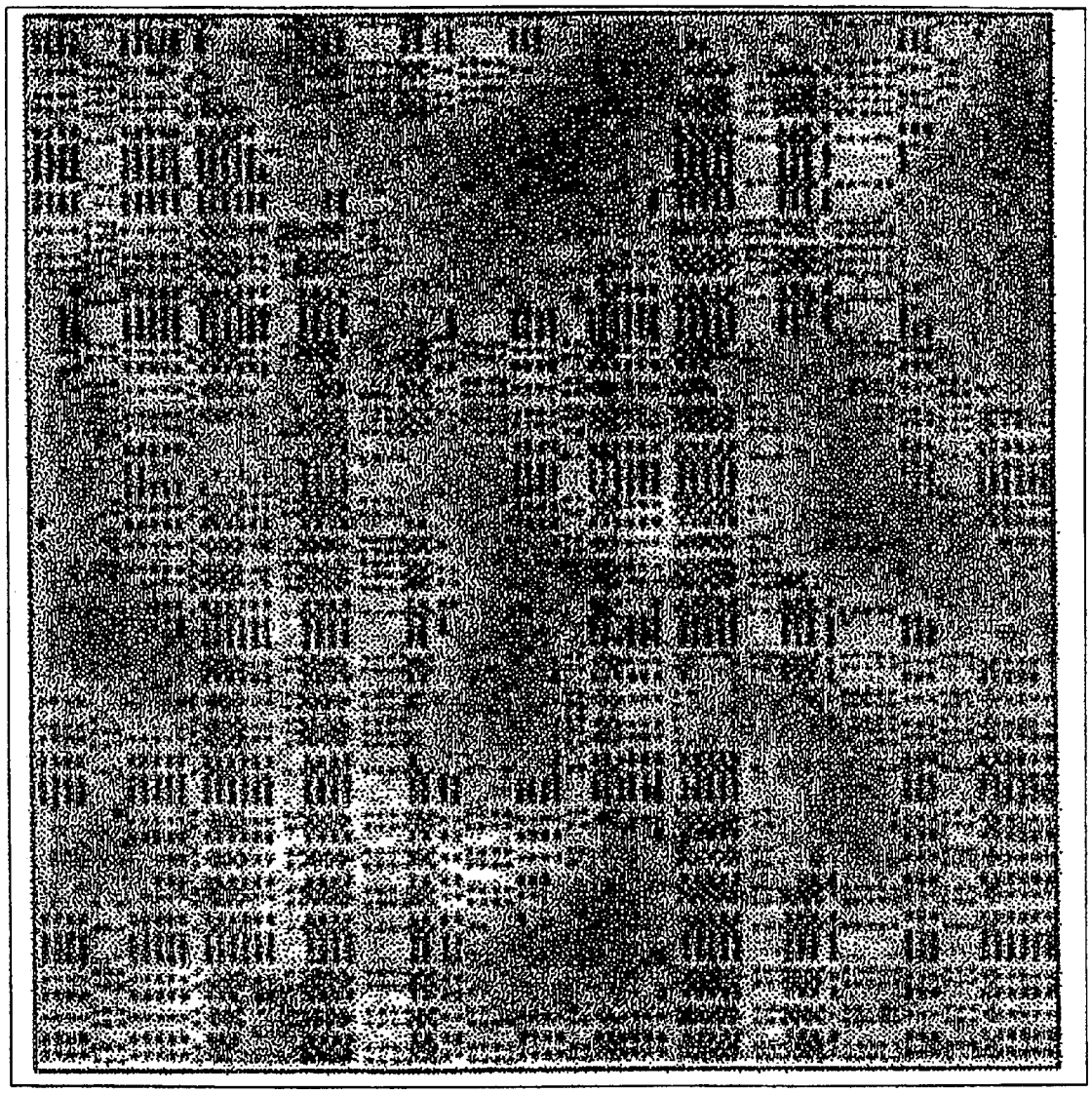
Figure 10C:
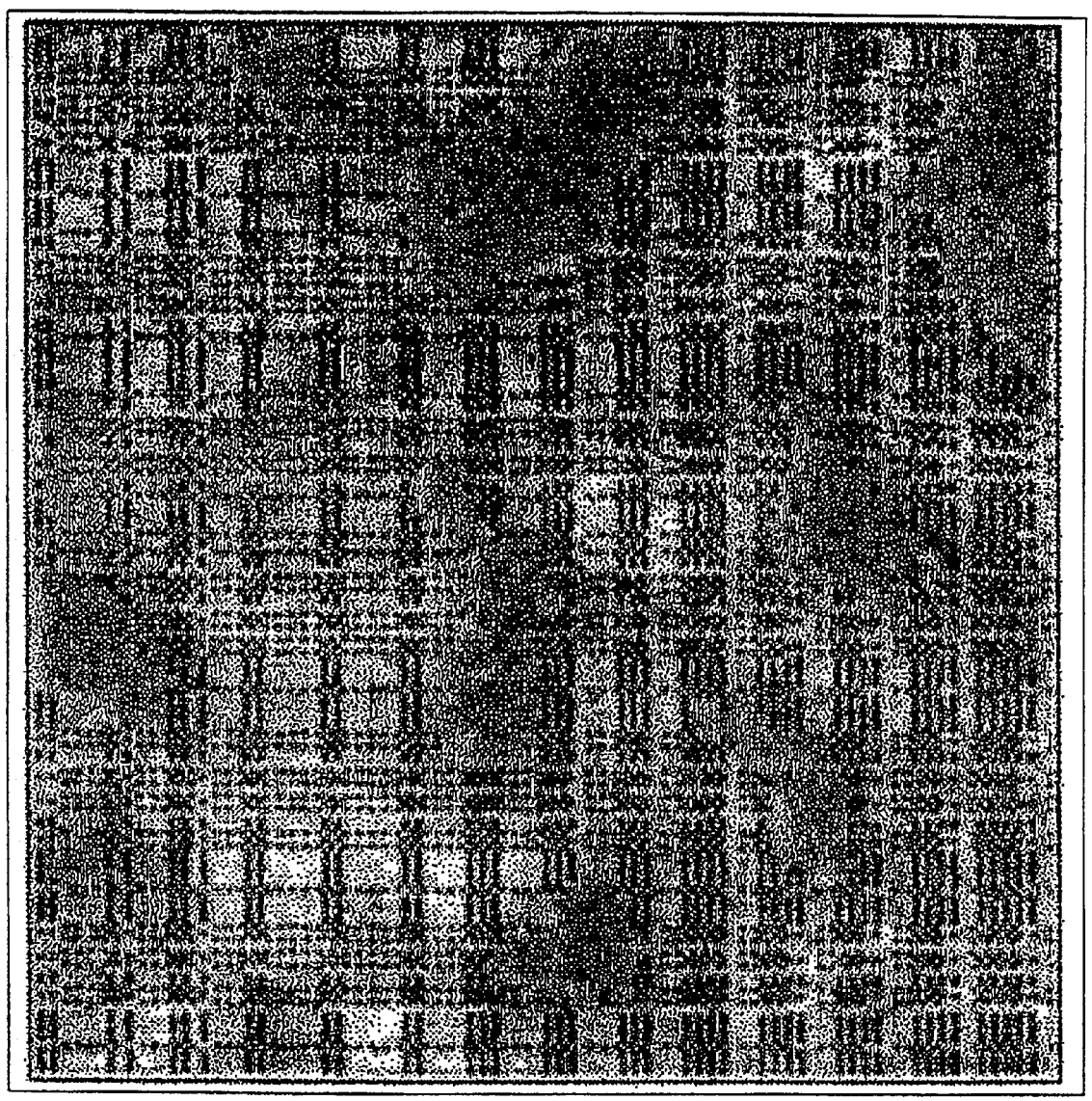

At step S40, the standardization process is performed, similar to step S18. At step S42, the number of the pixels of the image data is counted, similar to step S20. Finally, at step S44, the growth degree of the HSGs is calculated, similar to step S22. FIGS. 10A to 10C are exemplary views of images showing a calculated value of the growth degree of the HSGs and a growth state of the HSGs, respectively.

Figure 11A:
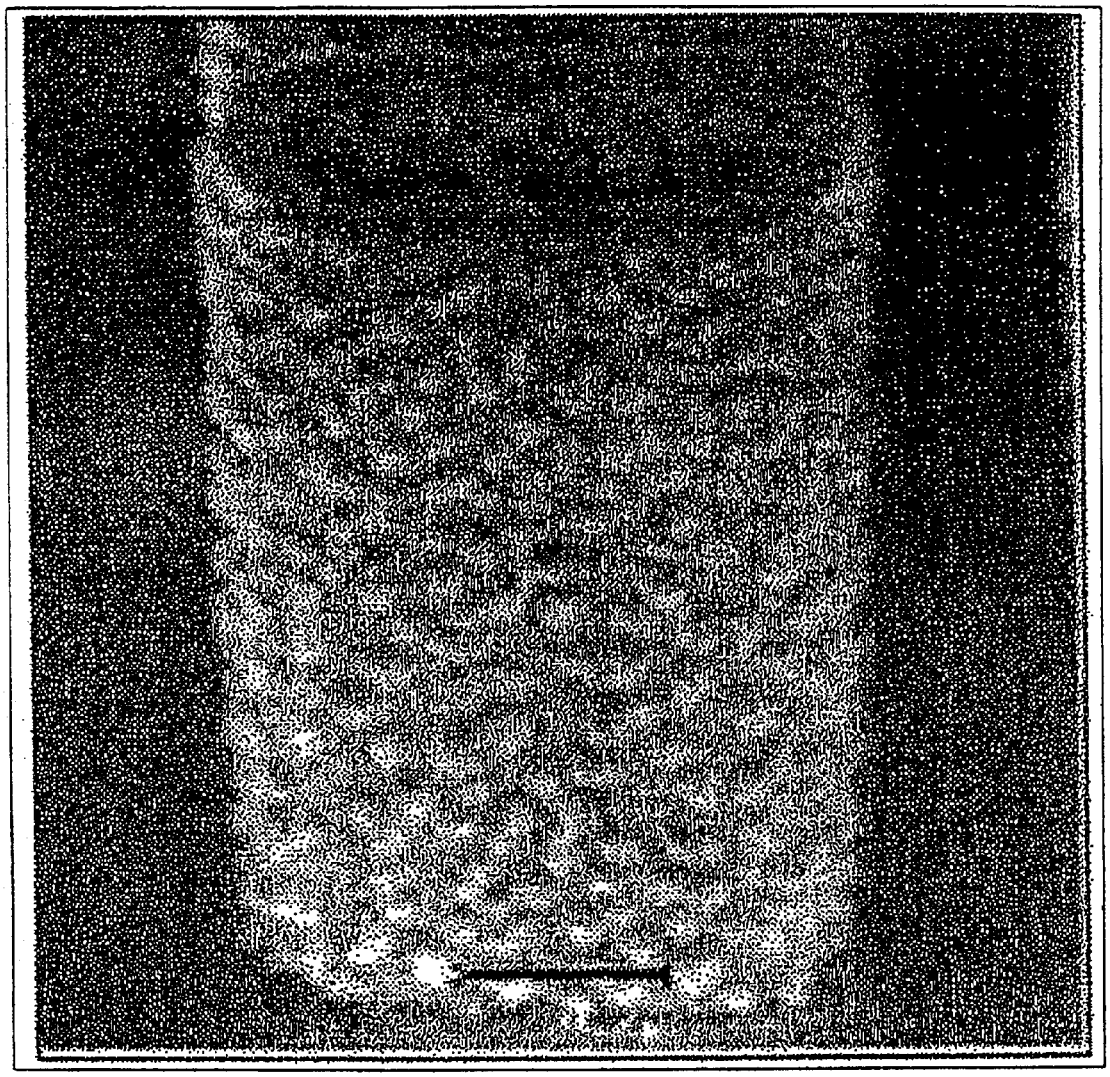
FIGS. 11A to 11C are exemplary views showing an SEM image and a calculated growth degree of the HSGs when the numerical algorithm is applied by setting a threshold value to 121.
Figure 11B:
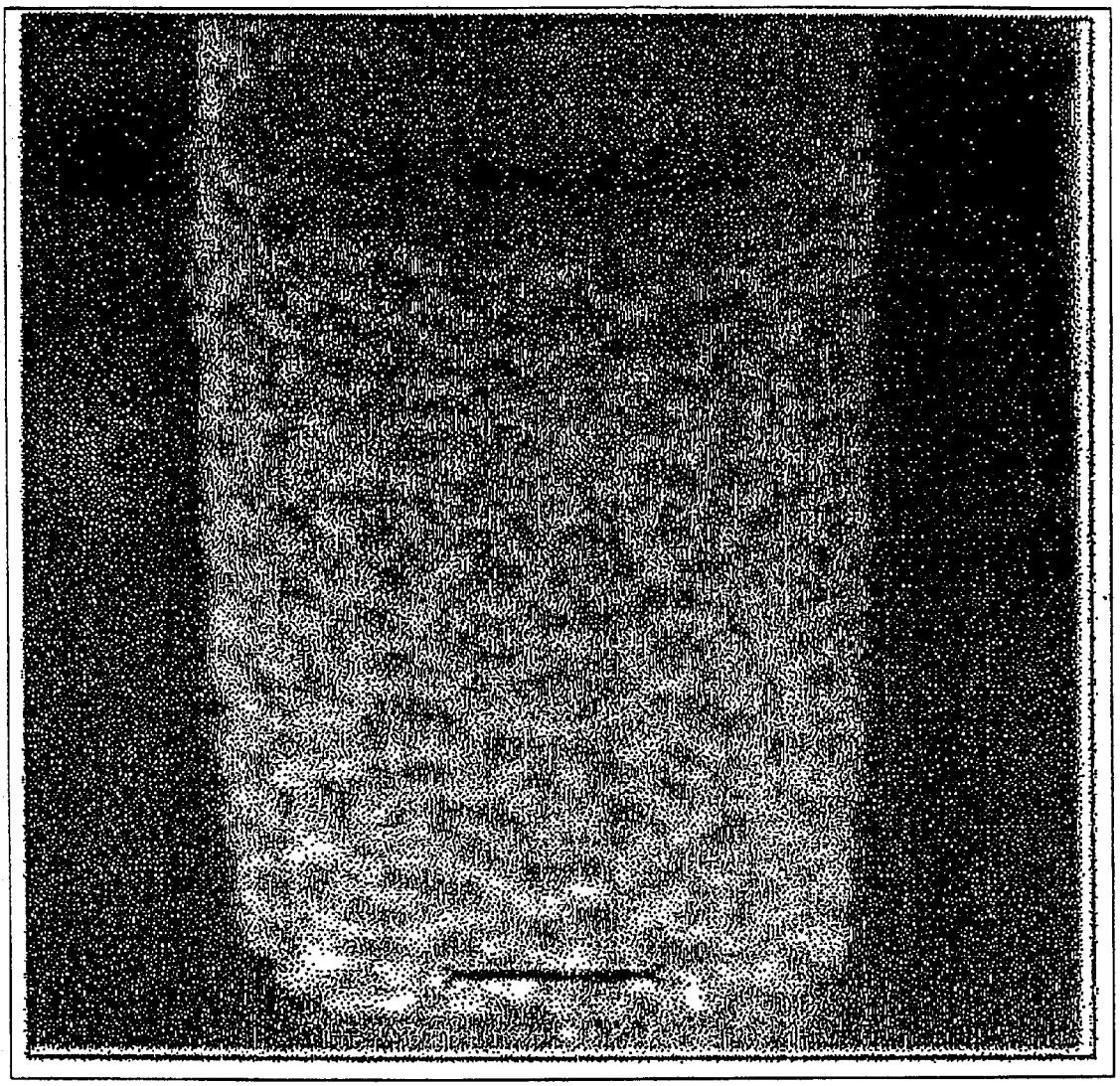
Figure 11C:
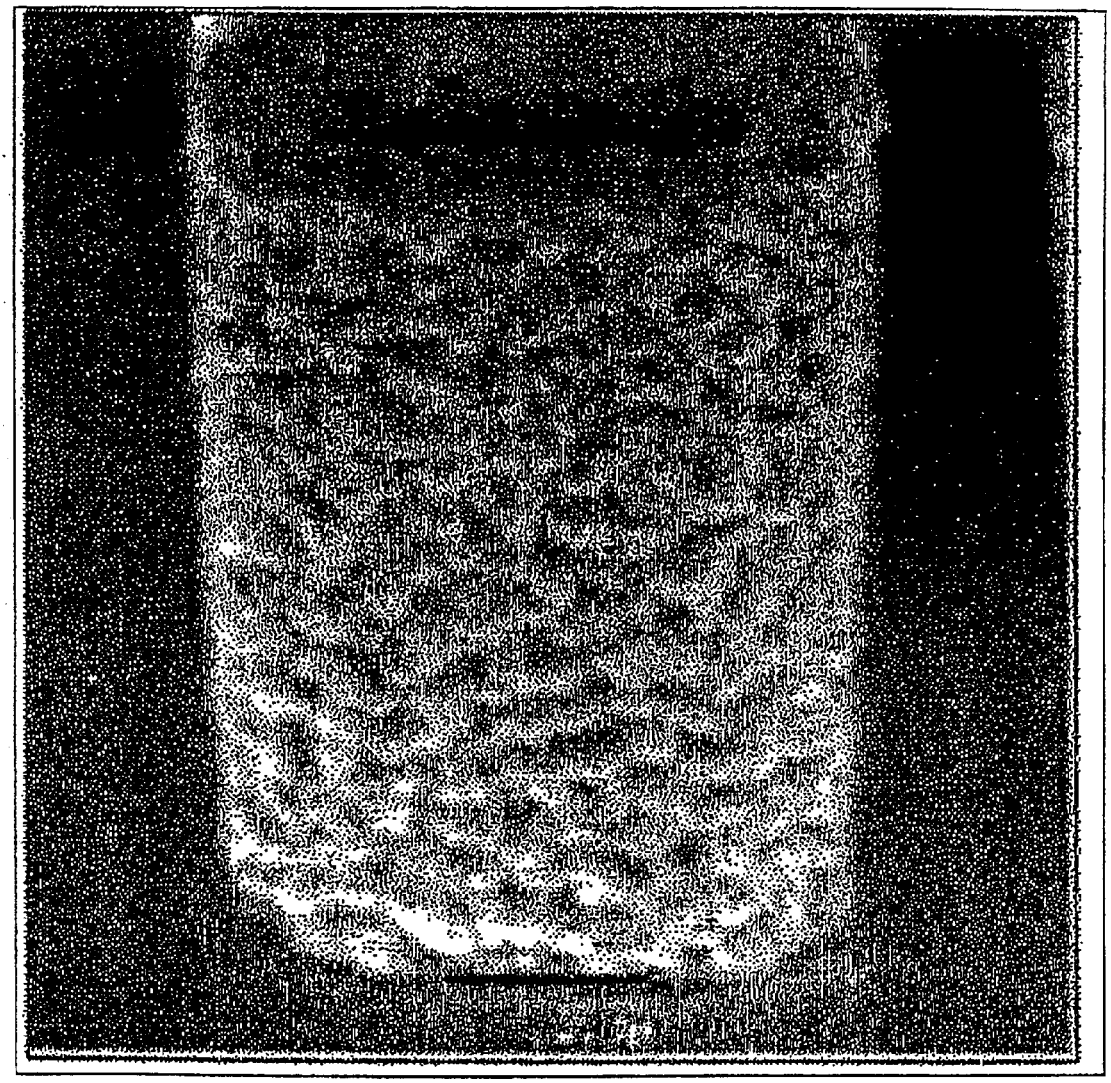

FIGS. 11A to 11C are views showing the SEM images and the calculated growth degree of the HSGs, when the numerical algorithm is applied setting the threshold value to 121 during the growth of the OCS-type capacitor cell under a predetermined growth condition. When 60 seconds, 100 seconds and 140 seconds are elapsed in the growth time of the HSGs, it can be seen that the HSGs are grown by about 36%, 54% and 66%, respectively.

Figure 12A:
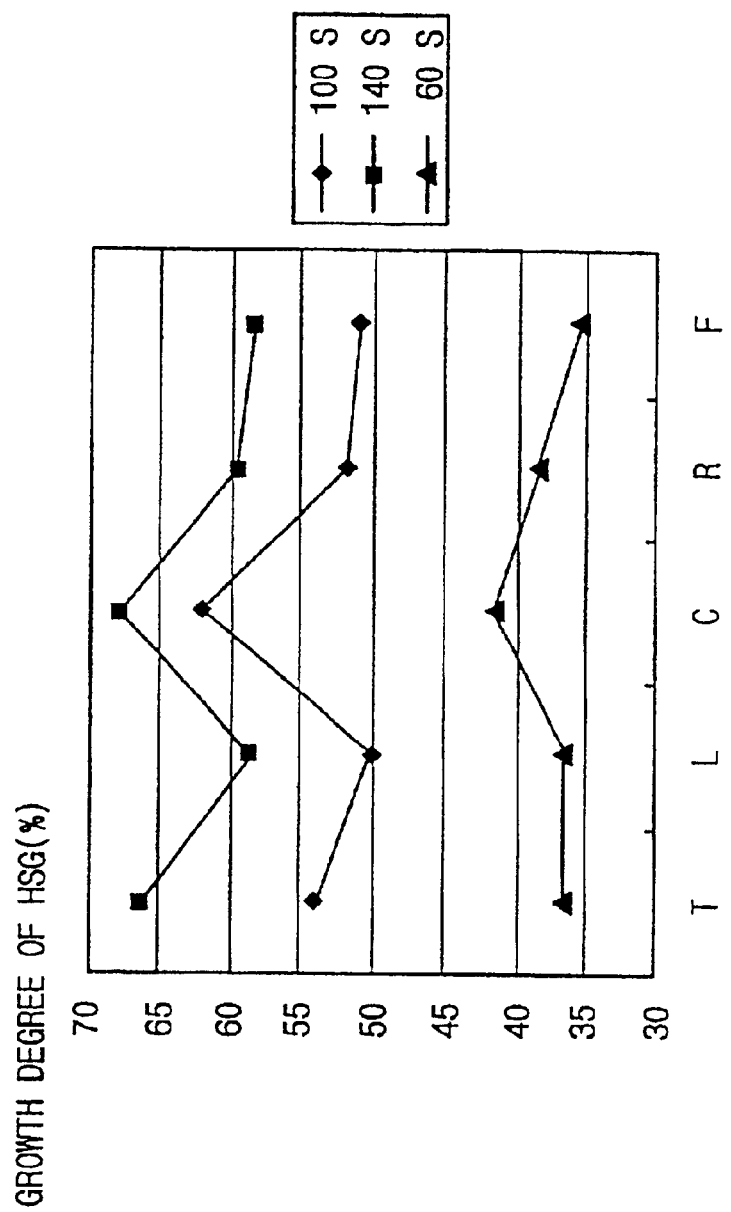
FIGS. 12A and 12B are graphs showing a calculated result of the growth degree of the HSGs according to a measuring portion of the semiconductor wafer and a growth time of the HSGs, respectively.
Figure 12B:
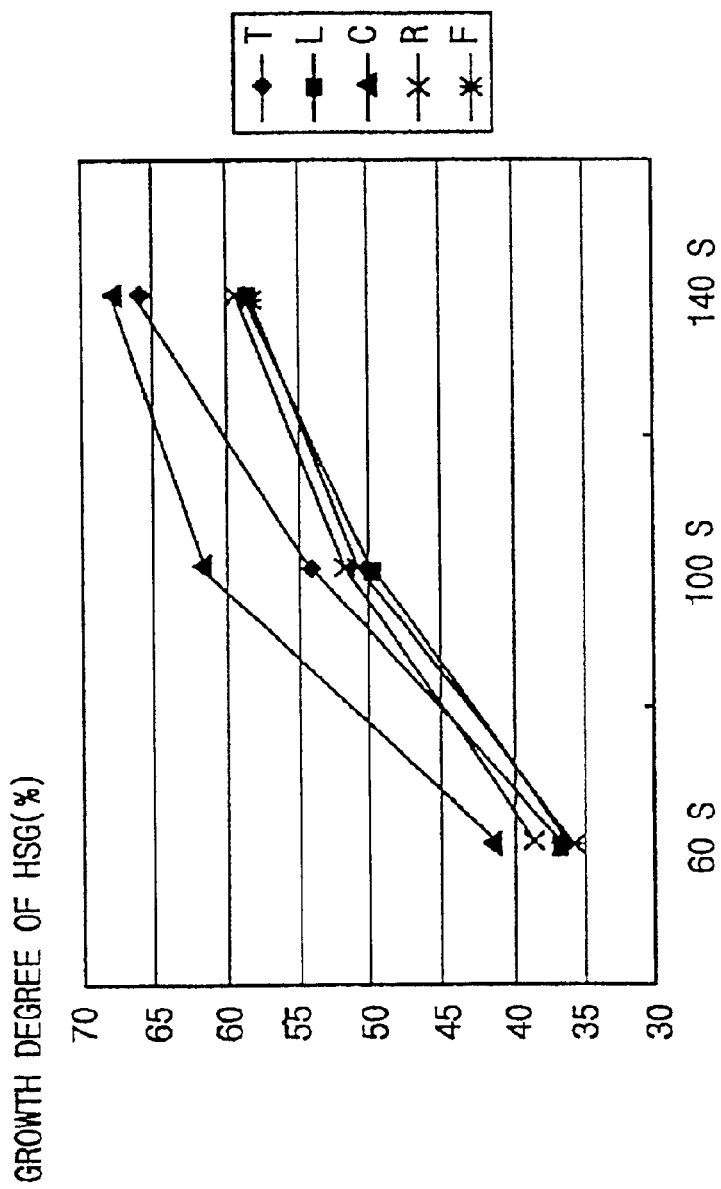

FIGS. 12A and 12B are graphs showing the calculated results of the growth degree of the HSGs according to the measured position of the semiconductor wafer and the growth time of the HSGs, respectively. In FIGS. 12A and 12B, reference symbols T, L, C, R and F represent that the measured position of the SEM image is the top, the left, the bottom, the right, and a flat zone, respectively.

Although the above described algorithms can be installed in the computer 38 having the SEM and can be operated in off-line mode, it is also possible to perform the numerical process in on-line mode through other computers integrated with a local access network (LAN). For this, an on-line service function is only added to the numerical program.

Although the method for numerating the growth degree of the HSGs in manufacturing the OCS-type capacitor cell is described as an embodiment of the present invention, the present invention can also be applied to numerate the distribution degree of unevenness with respect to a surface of a specimen using an SEM image of the specimen.

As mentioned above, the growth degree of grains on the surface of the specimen, e.g., the semiconductor wafer, captured using the SEM can be automatically calculated through the program, not the operator's visible observation.

Therefore, the analysis of the grain growth state can be achieved rapidly and accurately. As a result, the quality of devices is improved and the analysis time is reduced, thereby obtaining increased productivity.

While the present invention has been described in detail, it should be understood that various changes, substitutions and alterations could be made hereto without departing from the spirit and scope of the invention as defined by the appended claims.

What is claimed is:

1. A method for numerically analyzing a growth degree of grains on a surface of a semiconductor wafer, comprising:

selecting a numerical target zone in an image file for numerating the growth degree of grains on a specific portion of the surface of the semiconductor wafer, the image file being generated by scanning the specific portion on the surface of the semiconductor wafer using a scanning electron microscopy (SEM);

performing a standardization with respect to an image data of respective pixels disposed within the selected numerical target zone to obtain standardized image data values;

comparing the standardized image data values of the respective pixels with a predetermined threshold value;

counting a number of pixels of which a standardized image data value is greater than the threshold value; and numerating the growth degree of grains on the surface of the numerical target zone by calculating a ratio of the number of the counted pixels with respect to a number of total pixels disposed within the numerical target zone.

2. The method of claim 1, further comprising displaying the calculated ratio on a monitor.

3. The method of claim 1, further comprising, prior to performing the standardization with respect to the image data, employing a smoothing process for smoothing the image data of the respective pixels disposed within the numerical target zone using an average value of image data of adjacent pixels.

4. The method of claim 1, wherein the standardization is performed using a following equation:

$$NC_{ij} = \left( \frac{C_{ij} - C_{\min}}{C_{\max} - C_{\max}} \right) \times K$$

wherein, $NC_{ij}$ is a standardized image data value of a pixel disposed at a point (i,j), $C_{ij}$ a non-standardized image data value of the pixel disposed at the point (i,j), $C_{min}$ is a minimum value of image data within the numerical target zone, $C_{max}$ is a maximum value of image data within the numerical target zone, and K is a constant.

5. The method of claim 4, wherein the constant K is a number of total gradation of a monitor.

6. The method of claim 1, wherein the image file includes an image data obtained by scanning a growth state of hemispherical grains (HSGs) grown on a surface of a capacitor.

7. The method of claim 6, wherein the scanning is performed on a cylinder stack (OCS)—type capacitor.

8. The method of claim 7, wherein the scanning of the numerical target of the growth degree of grains includes scanning sidewalls of the OCS-type capacitor.

9. A method for numerically analyzing a growth degree of grains on a surface of a semiconductor wafer, comprising:

displaying an image on a monitor, the image being obtained by scanning a specific portion of the surface of the semiconductor wafer using a scanning electron microscopy (SEM);

manually selecting a numerical target zone in the displayed image in order to numerate the growth degree of grains on the specific portion of the surface of the semiconductor wafer;

performing a standardization with respect to an image data of respective pixels disposed within the selected numerical target zone to obtain standardized image data values;

comparing the standardized image data values of the respective pixels with a predetermined threshold value;

counting a number of pixels of which a standardized image data value is greater than the threshold value; and numerating the growth degree of grains on the surface of the numerical target zone by calculating a ratio of the number of the counted pixels with respect to a number of total pixels disposed within the numerical target zone.

10. The method of claim 9, wherein before manually selecting the numerical target zone, further comprising forming mesh lines dividing a screen of the monitor into a plurality of sub areas over the displayed image, thereby enabling an operator to select at least one sub area as the numerical target zone.

11. The method of claim 9, further comprising, prior to performing the standardization with respect to the image data, employing a smoothing process for smoothing the image data of the respective pixels disposed within the numerical target zone using an average value of image data of adjacent pixels.

12. The method of claim 11, further comprising replacing the image data of each of the respective pixels with an average value calculated from the image data of each of the respective pixels and that of pixels adjacent to each of the respective pixels.

13. The method of claim 9, wherein the standardization is performed using a following equation:

$$NC_{ij} = \left(\frac{C_{ij} - C_{\min}}{C_{\max} - C_{\max}}\right) \times K$$

wherein, $NC_{ij}$ is a standardized image data value of a pixel disposed at a point (i,j), $C_{ij}$ a non-standardized image data value of the pixel disposed at the point (i,j), $C_{min}$ is a minimum value of image data within the numerical target zone, $C_{max}$ is a maximum value of image data within the numerical target zone, and K is a constant.

14. The method of claim 13, wherein the constant K is the number of total gradation of the monitor.

15. The method of claim 9, wherein the image file includes an image data obtained by scanning a growth state of hemispherical grains (HSGs) grown on a surface of a capacitor.

16. The method of claim 15, wherein the scanning is performed on a cylinder stack (OCS)—type capacitor.

17. The method of claim 16, wherein the scanning of the numerical target of the growth degree of grains includes scanning sidewalls of the OCS-type capacitor.

18. An apparatus for numerically analyzing a growth degree of grains on a surface of a semiconductor wafer, comprising:

a scanning electron microscopy (SEM) for scanning a specific portion of the surface of the semiconductor wafer to generate an image signal;

an analog-to-digital converter for converting the image signal generated by the scanning electron microscopy (SEM) into digital data;

a computing device capable of (i) storing the digital data as an image file, (ii) opening the stored image file to automatically select a numerical target zone for numerating the growth degree of grains on the specific portion of the surface of the semiconductor device, (iii) performing a standardization with respect to image data of respective pixels disposed within the selected numerical target zone to obtain standardized image data values, (iv) comparing the standardized image data values of the respective pixels with a predetermined threshold value, (v) counting the number of pixels whose standardized image data value is greater than the threshold value, and (vi) numerating the growth degree of grains on the surface of the numerical target zone by calculating a ratio of the number of the counted pixels with respect to a number of total pixels disposed within the numerical target zone; and a display device for displaying the calculated ratio.

19. The apparatus of claim 18, wherein the computing device further comprises a capability for performing a smoothing process for smoothing the image data of respective pixels disposed within the numerical target zone using an average value of image data of adjacent pixels.

20. The apparatus of claim 18, wherein the standardization is performed by the computing device using a following equation:

$$NC_{ij} = \left(\frac{C_{ij} - C_{\min}}{C_{\max} - C_{\max}}\right) \times K$$

wherein, $NC_{ij}$ is a standardized image data value of a pixel disposed at a point (i,j), $C_{ij}$ a non-standardized image data value of the pixel disposed at the point (i,j), $C_{min}$ is a minimum value of image data within the numerical target zone, $C_{max}$ is a maximum value of image data within the numerical target zone, and K is a constant.

21. The apparatus of claim 20, wherein the constant K is the number of total gradation of the monitor.

22. The apparatus of claim 18, wherein the image file comprises image data obtained by scanning a growth state of hemispherical grains (HSGs) grown on a surface of a capacitor.

23. The apparatus of claim 22, wherein the capacitor is a cylinder stack (OCS)—type capacitor.

24. The apparatus of claim 23, wherein a numerical target of the growth degree of grains includes sidewalls of the OCS-type capacitor.

25. An apparatus for numerically analyzing a growth degree of grains on a surface of a semiconductor wafer, comprising:

a scanning electron microscopy (SEM) for scanning a specific portion of the surface of the semiconductor wafer to generate an image signal;

an analog-to-digital converter for converting the image signal generated by the scanning electron microscopy (SEM) into digital data;

a display device for receiving the image signal and displaying an image of the specific portion of the surface of the semiconductor wafer on a screen; and a computer device capable of (i) storing the digital data as an image file, (ii) forming mesh lines for dividing the screen into a plurality of sub areas over the displayed image of the specific portion of the surface of the semiconductor wafer, (iii) opening the stored image file to perform a standardization with respect to image data of respective pixels disposed within a numerical target zone that is manually selected by an operator by designating a predetermined sub area on the screen, (iv) comparing standardized image data values of the respective pixels with a predetermined threshold value, (v) counting the number of pixels whose standardized image data value is greater than the threshold value, (vi) numerating the growth degree of grains on the surface of the numerical target zone by calculating a ratio of the number of the counted pixels with respect to a number of total pixels disposed within the numerical target zone, and (vii) providing the calculated ratio to the display device to thereby display the calculated ratio on the screen.

26. The apparatus of claim 25, wherein the computing device further comprises a capability for performing a smoothing process for smoothing the image data of respective pixels disposed within the numerical target zone using an average value of image data of adjacent pixels.

27. The apparatus of claim 25, wherein the standardization is performed using a following equation:

$$NC_{ij} = \left(\frac{C_{ij} - C_{\min}}{C_{\max} - C_{\max}}\right) \times K$$

wherein, $NC_{ij}$ is a standardized image data value of a pixel disposed at a point (i,j), $C_{ij}$ a non-standardized image data value of the pixel disposed at the point (i,j), $C_{min}$ is a minimum value of image data within the numerical target zone, $C_{max}$ is a maximum value of image data within the numerical target zone, and K is a constant.

28. The apparatus of claim 27, wherein the constant K is the number of total gradation of the monitor.

29. The apparatus of claim 25, wherein the image file comprises image data obtained by scanning a growth state of hemispherical grains (HSGs) grown on a surface of a capacitor.

30. The apparatus of claim 29, wherein the capacitor is a cylinder stack (OCS)-type capacitor.

31. The apparatus of claim 30, wherein a numerical target of the growth degree of grains includes sidewalls of the OCS-type capacitor.

* * * * *